United States Patent
Khatib et al.

(10) Patent No.: US 6,237,430 B1
(45) Date of Patent: May 29, 2001

(54) PROCESS FOR SAMPLING OPEN WATER SHEEN

(75) Inventors: Zara Ibrahim Khatib, Rijswijk (NL); Darrell Elliott Way, Katy, TX (US); Gregory Hamilton Hardy, Mandeville, LA (US); Ileana Aurea Leon Rhodes, Katy, TX (US); Louis Patrick Bruzuzy, Humble, TX (US); Bela Michael James; Madorom Evelyn Huot, both of Houston, TX (US); Jane Graham Price, Abita Springs, LA (US)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 09/439,022

(22) Filed: Nov. 12, 1999

Related U.S. Application Data

(60) Provisional application No. 60/108,554, filed on Nov. 16, 1998.

(51) Int. Cl.$^7$ .................................................. G01N 1/00
(52) U.S. Cl. .......................................................... 73/864.72
(58) Field of Search ................................. 73/863, 864.31, 73/864.51, 864.63–864.67, 864.72, 864.91

(56) References Cited

U.S. PATENT DOCUMENTS

| | | | | |
|---|---|---|---|---|
| 4,157,664 | * | 6/1979 | Robinson | 73/864.66 |
| 5,284,048 | * | 2/1994 | Horner | 73/864.72 |
| 5,676,839 | * | 10/1997 | Shippert . | |
| 5,885,451 | * | 3/1999 | Porrovecchio, Sr. . | |

* cited by examiner

*Primary Examiner*—Robert Raevis
(74) *Attorney, Agent, or Firm*—Beverlee G. Steinberg

(57) ABSTRACT

There is provided a method for collecting sheen samples from open water, the method comprising providing a collection device for sampling sheen; casting the collection device into open water containing sheen; collecting a sheen sample; and retrieving the collection device.

13 Claims, No Drawings

PROCESS FOR SAMPLING OPEN WATER SHEEN

This application claims the benefit of U.S. Provisional Application No. 60/108,554, filed Nov. 16, 1998, the entire disclosure of which is hereby incorporated by reference.

FIELD OF THE INVENTION

The invention relates to a process for collecting sheen samples, particularly sheen samples from open water.

BACKGROUND OF THE INVENTION

Sheen occurs in open water such as near offshore platforms, in harbors, lakes canals or the like. Sheen may be due, for example, to natural seeps, offshore discharges (such as produced water, sump, or completion or workover fluids) and pipeline leaks or due to a chemical spill. It may also be caused by runoff from industrial locations to open water canals or rivers. It becomes necessary to collect samples of the sheen off the water in order to evaluate the cause of the sheen and develop a solution to prevent further sheen.

Collection of sheen samples, however, may be difficult using commonly available methods and apparatus. For example, the floor of a platform may be quite far above the surface of the water and the sheen, many times necessitating the need for a boat to collect samples. Sheen may also collect in areas which are difficult to reach, even by boat. Sheens are generally very thin layers, only microns thick. A common method of taking a sample is to dip a container into the water. However, taking a sample by a container causes the dissipation of the sheen and prevents the collection of enough volume necessary for analysis.

Some solutions to the container sampling problem is seen by using collection devices such, as glass plates and solvent pads, both of which are dipped into the sheen, Teflon drums, which are rolled in the sheen, Teflon tape, and polypropylene tape attached to a rake. Each of these has disadvantages, particularly when collecting from a platform or a boat on rough waters.

SUMMARY OF THE INVENTION

There is provided a method for collecting sheen samples from open water, said method comprising providing a collection device for sampling sheen; casting said collection device into open water containing sheen; collecting a sheen sample; and retrieving said collection device.

DETAILED DESCRIPTION OF THE INVENTION

The process of the invention provides the ability to collect sheen samples from the floor of a platform, from a boat, even in rough water, or from an area away from the launching point.

The sampling process comprises placing a sampler on a line and casting the sampler and the line into water containing sheen, then retrieving the sampler after it has contacted and collected a sample of the sheen. A particularly effective sampler is an absorbent compatible with the nature of the sheen being sampled. The sampler should float on water, since sheen is typically surface oriented. A preferable absorbent is in tape form, such as 1 to 2 mm tape, or high surface area fibers. The material of the absorbent is dependent upon the sheen to be sampled and may be selected from a chemically treated polypropylene, tetrafluoroethylene, polytetrafluoroethylene, or other absorbents that are compatible with the nature of the sheen being sampled, and combinations thereof. The tape or fibers may be loosely wound into a castable shape, such as the shape of a fishing lure. In order to maintain the castable shape, the tape or fibers may be further wrapped in a destructible or dissolvable wrap, such as water soluble paper. A means for attaching the absorbent to the line may be incorporated into the shaped absorbent. When cast into the water, the destructible wrap falls away, self-destructs or dissolves, allowing the tape or fibers to unravel and expose the maximum absorbent surface area to the sheen. Since sheens are typically oriented on the surface of the water, it is preferable if the absorbent floats on the sheen and adsorbs the sheen's components, such as oil base components. The sampler is then retrieved, placed in a sample jar and sent for analysis.

The shaped and possibly wrapped absorbent is attached to a line and a means for casting. The line may be common fishing line and the means for casting may be a common fishing rod, although other casting means, including motorized means, may be used. The means for connecting the absorbent to the line may be any means which produces a secure connection. If the absorbent is shaped into the shape of a fishing lure, for example, the means to connect the absorbent to the line could be an eye which is incorporated into the lure shape and to which the line is tied.

Other embodiments of the invention will be apparent to those skilled in the art from a consideration of this specification or from practice of the invention disclosed. It is intended that the specification be considered as exemplary only, with the true scope and spirit of the invention being indicated by the following claims.

We claim:

1. A method for collecting sheen samples from open water, said method comprising providing a collection device for sampling sheen; casting said collection device into open water containing sheen; collecting a sheen sample; and retrieving said collection device; wherein said collection device comprises an absorbent that floats on the water, thereby absorbing the components of the sheen upon contact; and wherein said absorbent is wrapped in a destructible wrap.

2. A method according to claim 1 wherein said absorbent comprises a tape or high surface area fibers.

3. A method according to claim 2 wherein said tape or high surface area fibers is selected from chemically treated polypropylene, tetrafluoroethylene, polytetrafluoroethylene, absorbents compatible with said sheen, and combinations thereof.

4. A method according to claim 1 wherein said collection device comprises an absorbent, a line, a means for connecting said absorbent to said line, and a means for casting said absorbent and said line into water.

5. A method according to claim 4 wherein said absorbent is attached to a fishing rod and said fishing rod is used to cast said collection device into open water.

6. A method according to claim 4 wherein said absorbent comprises a tape or high surface area fibers.

7. A method according to claim 6 wherein said tape or high surface area fibers is selected from chemically treated polypropylene, tetrafluoroethylene, polytetrafluoroethylene, absorbents compatible with said sheen, and combinations thereof.

8. A method according to claim 1 wherein said wrap is a water soluble paper.

9. A method for collecting sheen samples from open water, said method comprising providing a collection device for sampling sheen; casting said collection device into open water containing sheen; collecting a sheen sample; and retrieving said collection device; wherein said collection device comprises an absorbent, a line, a means for connecting said absorbent to said line, and a means for casting said absorbent and said line into water; and wherein said absorbent is wrapped in destructive wrap.

10. A method according to claim 9 wherein said absorbent is attached to a fishing rod and said fishing rod is used to cast said collection device into open water.

11. A method according to claim 9 wherein said absorbent comprises a tape or high surface area fibers.

12. A method according to claim 11 wherein said tape or high surface area fibers is selected from chemically treated polypropylene, tetrafluoroethylene, polytetrafluoroethylene, absorbents compatible with said sheen, and combinations thereof.

13. A method according to claim 9 wherein said wrap is a water soluble paper.

* * * * *